(12) United States Patent
Hundt et al.

(10) Patent No.: US 10,111,504 B2
(45) Date of Patent: Oct. 30, 2018

(54) WEARABLE DEVICE AND WRISTBAND THEREOF

(71) Applicant: HTC CORPORATION, Taoyuan (TW)

(72) Inventors: Daniel Hundt, San Francisco, CA (US); Nichole Suzanne Rouillac, San Francisco, CA (US); Kristina Nicole Marrero, San Francisco, CA (US); Robin Nicholas Hubbard, San Francisco, CA (US); Mathias Andreas Hintermann, San Francisco, CA (US); Lawrence Herman Fong, San Francisco, CA (US); Michael Che Ho Keogan Lo, San Francisco, CA (US); Stuart Kyle, San Francisco, CA (US); Hsin-Hao Lee, Taoyuan (TW); Han-Wen Yeh, Taoyuan (TW)

(73) Assignee: HTC CORPORATION, Taoyuan (TW)

( * ) Notice: Subject to any disclaimer, the term of this patent is extended or adjusted under 35 U.S.C. 154(b) by 0 days.

(21) Appl. No.: 15/649,948

(22) Filed: Jul. 14, 2017

(65) Prior Publication Data
US 2018/0020785 A1   Jan. 25, 2018

Related U.S. Application Data

(60) Provisional application No. 62/366,189, filed on Jul. 25, 2016.

(51) Int. Cl.
*A44C 5/00* (2006.01)
*A61B 5/024* (2006.01)
(Continued)

(52) U.S. Cl.
CPC ........ *A44C 5/0053* (2013.01); *A61B 5/02438* (2013.01); *G08B 5/228* (2013.01); *H04B 2001/3861* (2013.01)

(58) Field of Classification Search
CPC .. A44C 5/0053; A61B 5/02438; G08B 5/228; H04B 2001/3861
See application file for complete search history.

(56) References Cited

U.S. PATENT DOCUMENTS

D742,875 S * 11/2015 Ji .................................. D10/32
D788,627 S *  6/2017 Park ............................... D11/5
(Continued)

FOREIGN PATENT DOCUMENTS

CN    103083889 A    5/2013
CN    104146771 A    11/2014

*Primary Examiner* — Corey Skurdal
(74) *Attorney, Agent, or Firm* — Birch, Stewart, Kolasch & Birch, LLP

(57) ABSTRACT

A wearable device, which comprises a wristband, an electronic module and a connector. The wristband comprises a housing and a band. The housing has a first end, a second end, and an accommodating space. The band has a first end extending from the first end of the housing, and a free second end opposite to the first end of the band. The electronic module disposes within the accommodating space. The connector disposes either at the second end of the housing, or at a first end of the electronic module that is closer to the second end of the housing than the first end of the housing, wherein the free second end of the band is insertable through or into the connector. Wherein there is free of any band between the second end of the housing and the connector and between the first end of the electronic module and the connector.

9 Claims, 17 Drawing Sheets

(51) Int. Cl.
*H04B 1/3827* (2015.01)
*G08B 5/22* (2006.01)

(56) References Cited

U.S. PATENT DOCUMENTS

| | | | | |
|---|---|---|---|---|
| D792,888 S | * | 7/2017 | Herrmann | D14/480.3 |
| 2007/0066088 A1 | * | 3/2007 | Rambosek | H05K 5/0278 439/37 |
| 2008/0041898 A1 | * | 2/2008 | Chou | A45C 13/008 224/219 |
| 2014/0174958 A1 | * | 6/2014 | Martinez | G06F 15/00 206/37 |
| 2016/0021771 A1 | * | 1/2016 | Zhang | G06F 1/163 361/752 |
| 2016/0116940 A1 | * | 4/2016 | Jones | G06F 1/163 361/679.03 |
| 2016/0290624 A1 | * | 10/2016 | Dai | A44C 5/0053 |
| 2016/0346609 A1 | * | 12/2016 | Bailly | A63B 24/0062 |
| 2017/0102131 A1 | * | 4/2017 | Chen | F21V 15/01 |
| 2017/0261335 A1 | * | 9/2017 | Hoffman | G04F 10/00 |

* cited by examiner

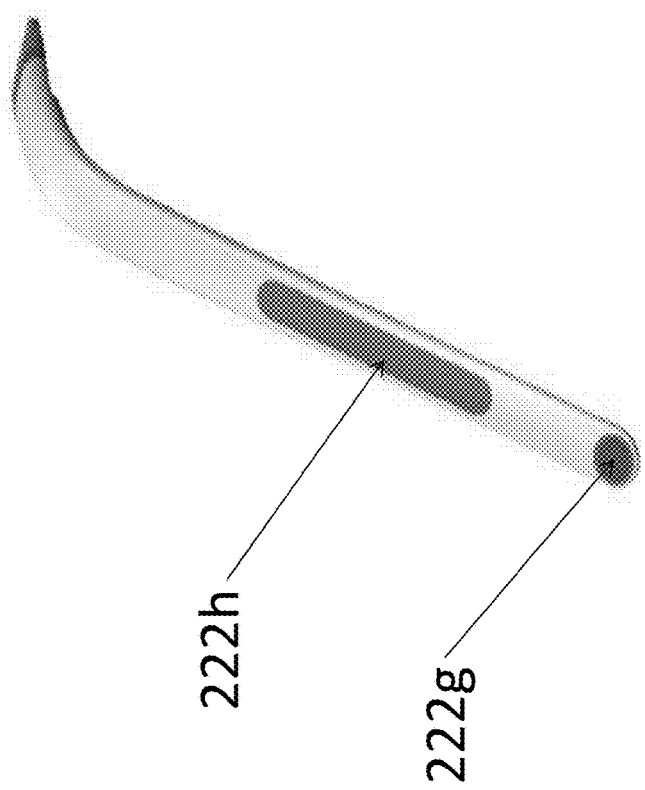

WEARABLE DEVICE AND WRISTBAND THEREOF

CROSS REFERENCE TO RELATED APPLICATIONS

This non-provisional application claims the benefit under 35 U.S.C. § 119(e) to U.S. Provisional Application No. 62/366,189, filed on Jul. 25, 2016, which is hereby expressly incorporated by reference into the present application.

BACKGROUND

Field of Invention

The present application relates to a wearable device and a wristband thereof. More particularly, the present application relates to a wearable device and a wristband thereof that can provide the users with new and diversified wearing experiences of the wearable device.

Description of Related Art

Recently, wearable devices (e.g., smart watches, smart wristbands, etc.) are popular due to their mobility and various functions. Wearable devices are utilized for measuring heart rates, tracking running routes, recording motion histories of users, displaying notifications to users, and/or providing other different functions. In order to offer the consumer a different choice of the wearable device, a different type of the wearable device is needed.

However, all of the existing wearable devices on the market only offer one type similar to a traditional watch, which has a processing module disposed in the middle portion of a wristband and two bands respectively extending from the two ends of the middle portion of the wristband.

SUMMARY

An aspect of the present disclosure is to provide a wearable device, which comprises a wristband, an electronic module and a connector. The wristband comprises a housing and a band. The housing has a first end, a second end, and an accommodating space which is between the first end and the second end. The band has a first end which is extending from the first end of the housing, and a free second end which is opposite to the first end of the band. The electronic module disposes within the accommodating space. The connector disposes either at the second end of the housing, or at a first end of the electronic module that is closer to the second end of the housing than to the first end of the housing, wherein the free second end of the band is insertable through or into the connector to fix the band to the connector. Wherein there is free of any band between the second end of the housing and the connector and between the first end of the electronic module and the connector.

Another aspect of the present disclosure is to provide a wristband, which is suitable for a wearable device. The wristband comprises a housing and a band. The housing has a first end, a second end, and an accommodating space between the first end and the second end. The band extends from the first end of the housing. Wherein the second end of the housing is free of any band.

BRIEF DESCRIPTION OF THE DRAWINGS

The disclosure can be more fully understood by reading the following detailed description of the embodiments, with reference made to the accompanying drawings as follows:

FIG. 17 is a schematic diagram illustrating how the band fixed to the connector according to another embodiment of the disclosure.

DETAILED DESCRIPTION

Figure 1:
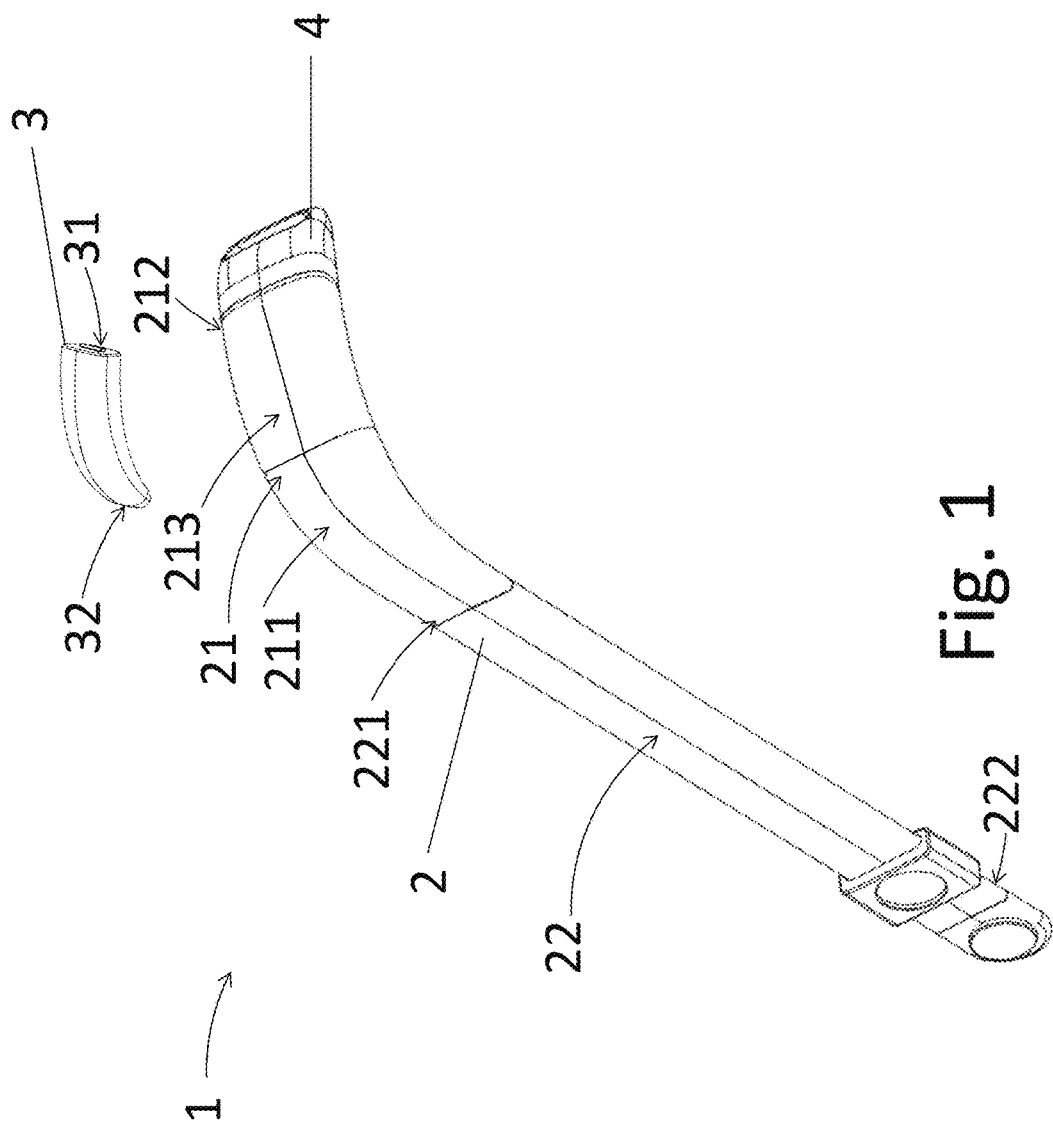
FIG. 1 is a schematic diagram illustrating a wearable device according to a first embodiment of the disclosure.

The following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a schematic diagram illustrating a wearable device 1 according to the first embodiment of the disclosure. As shown in FIG. 1, the wearable device 1 includes a wristband 2, an electronic module 3 and a connector 4.

In an embodiment, the wristband 2 is a flexible band, which is used to circle around the wrist of the user and comprises a housing 21 and a band 22. The housing 21 comprises a first end 211, a second end 212 and an accommodating space 213 between the first end 211 and the second end 212. The band 22 comprises a first end 221 extending from the first end 211 of the housing 21 and a free second end 222 opposite to the first end 221 of the band 22; that is to say, the second end 212 of the housing 21 is free of any band. In some embodiments, the surface material of the wristband 2 can be, but not limited to, fabric, rubber, plastic or other similar material to make the user to have a different touch, and the inner material of the wristband 2 can be, but not limited to, rubber, Thermoplastic Polyurethane (TPU), silicone or other similar material to make sure that the wristband 2 has enough flexibility to be folded.

In one embodiment, the electronic module 3 is a multi-function module which is used to offer the user different functions and disposed within the accommodating space 213. In this embodiment, the electronic module 3 is pre-disposed within the accommodating space 213 before sold to the customers. The electronic module 3 comprises a first end 31 and a second end 32, wherein the first end 31 of the electronic module 3 is closer to the second end 212 of the housing 21 than to the first end 211 of the housing 21. In an embodiment, the electronic module 3 further comprises a wireless communicating module and a vibration module, wherein the wireless communicating module is used to communicate with other device(s) such as a mobile phone, a computer or other similar smart devices through wireless technologies such as Wi-Fi, Bluetooth, etc., and the vibration module is used to inform the user of some events through the wireless communicating module.

Figure 2:
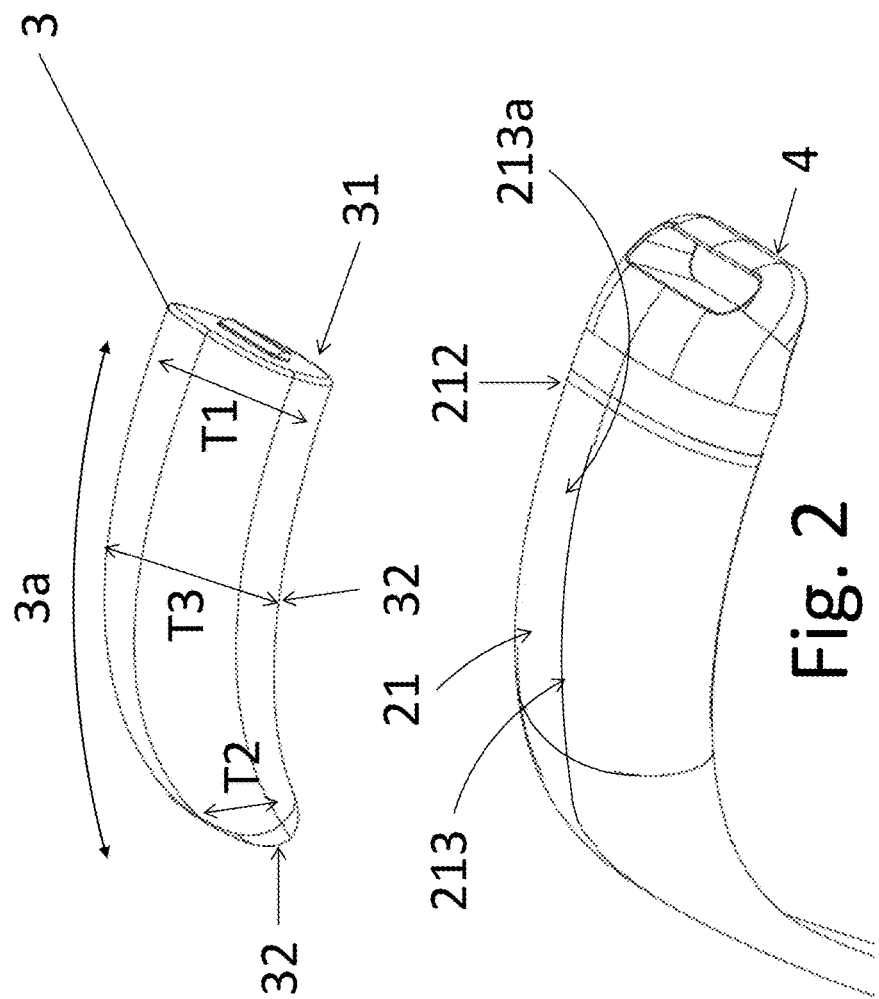
FIG. 2 is a section schematic diagram illustrating a wearable device according to a first embodiment of the disclosure.

FIG. 2 illustrates the assembly diagram of the electronic module of the first embodiment. The electronic module 3 comprises a curved surface 3a corresponding to an inner surface 213a of the accommodating space 213; that is to say, the electronic module 3 is disposed within the accommodating space 213 closely to avoid unnecessary collision between the electronic module 3 and the accommodating space 213. In this embodiment, the electronic module 3 has a first thickness T1 at the first end 31 of the electronic module 3, a second thickness T2 at the second end 32 of the electronic module 3, and a third thickness T3 at a central part 33 of the electronic module 3 which is between the first end 31 and the second end 32 of the electronic module 3, wherein the third thickness T3 is greater than the first thickness T1 and the second thickness T2, and the first thickness T1 is greater than or equal to the second thickness T2. As described above, the curved inner surface 213a of the accommodating space 213 corresponds to the curved shape of the electronic module 3. Further, since the third thickness T3 is greater than the first thickness T1 and the second thickness T2, it is easier to assemble the electronic module 3 into the accommodating space 213.

In some embodiments, the connector 4 is disposed either at the second end 212 of the housing 21, or at the first end 31 of the electronic module 3 that is closer to the second end 212 of the housing 21 than to the first end 211 of the housing 21, wherein the free second end 222 of the band 22 is insertable through or into the connector 4 to fix the band 22 to the connector 4. In this illustrated embodiment as shown in FIG. 2, the connector 4 is disposed at the second end 212 of the housing 21 since the electronic module 3 is entirely within the accommodating space 213. In this embodiment, there is free of any band between the second end 212 of the housing 21 and the connector 4.

Figure 3:
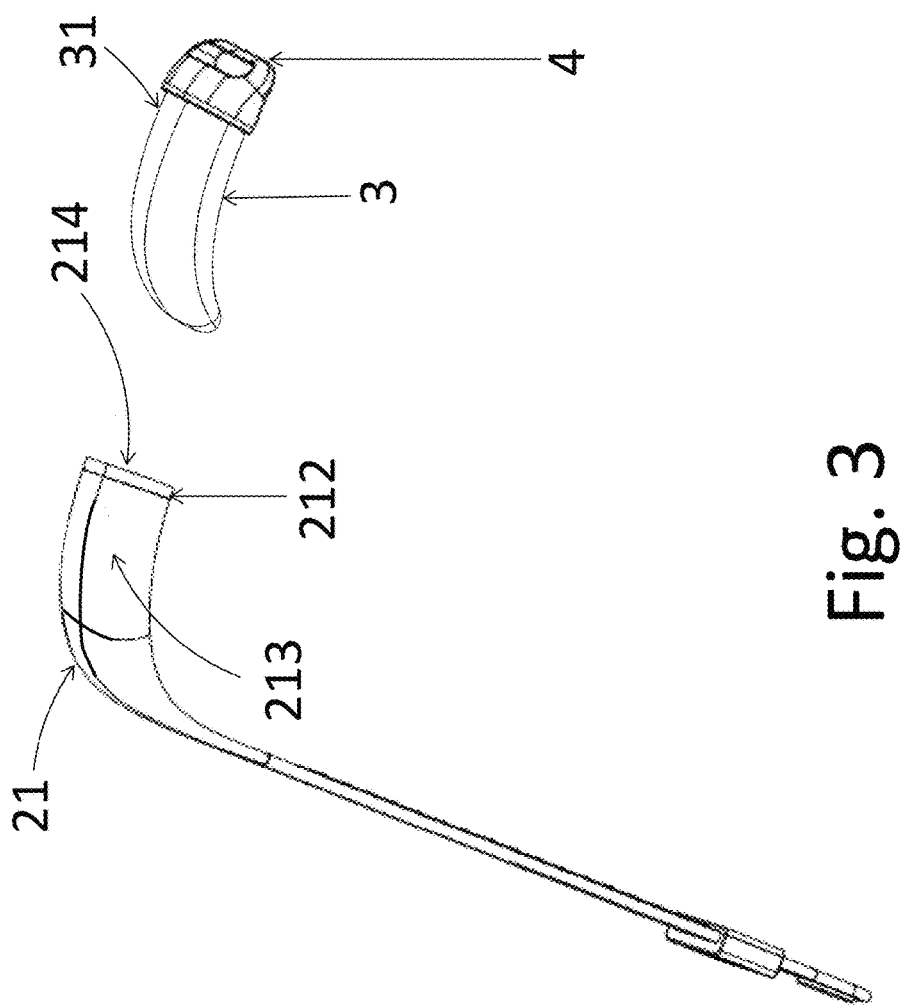
FIG. 3 is a schematic diagram illustrating a wearable device according to a second embodiment of the disclosure.
Figure 4:
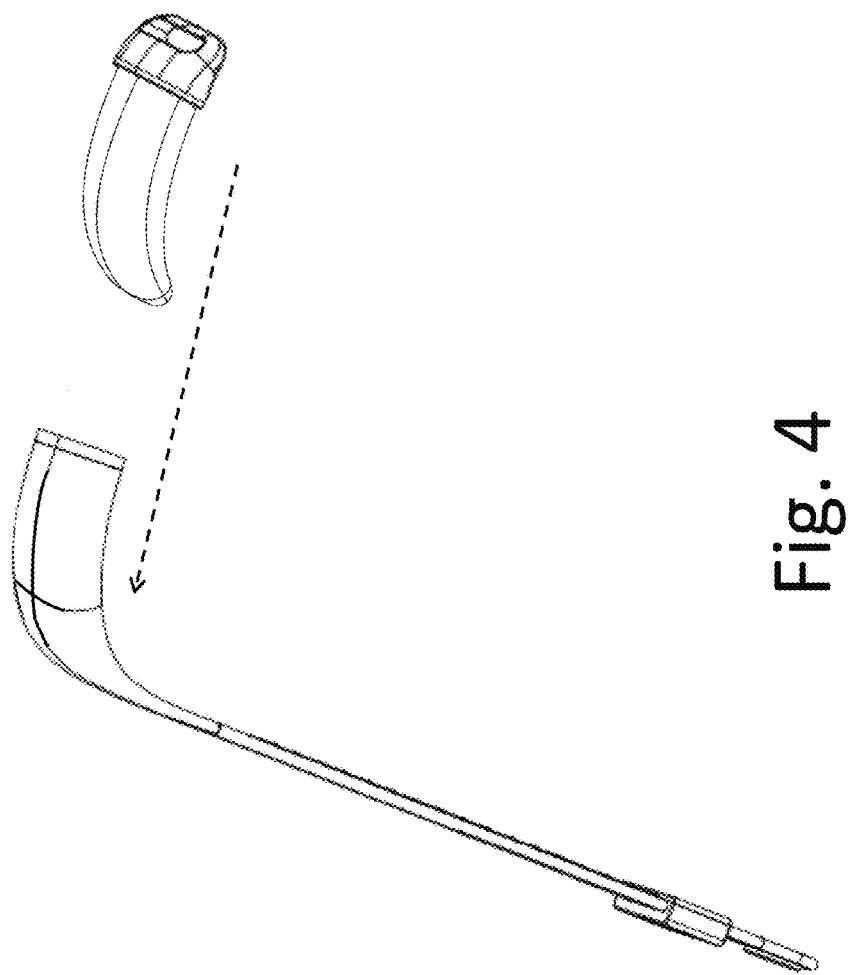
FIG. 4 is a schematic diagram illustrating a assembling process of a wearable device according to a second embodiment of the disclosure.

FIG. 3 illustrates a second embodiment of the wearable device and the FIG. 4 illustrates the assembling process of the wearable device of the second embodiment.

In an embodiment, the housing 21 further comprises a first opening 214 at the second end 212 to let the electronic module 3 be insertable into and removable from the accommodating space 213 through the first opening 214. The connector 4 is disposed at the first end 31 of the electronic module 3 and is exposed out of the accommodating space 213 through the first opening 214 when the electronic module 3 is inserted into the accommodating space 213. In this embodiment, there is free of any band between the first end 31 of the electronic module 3 and the connector 4.

In an embodiment, when the free second end of the band is inserted through or into the connector and fixes the band to the connector to form a ring, the housing of the wristband has an outer surface facing toward the ring and an inner surface opposite to the outer surface.

Figure 5:
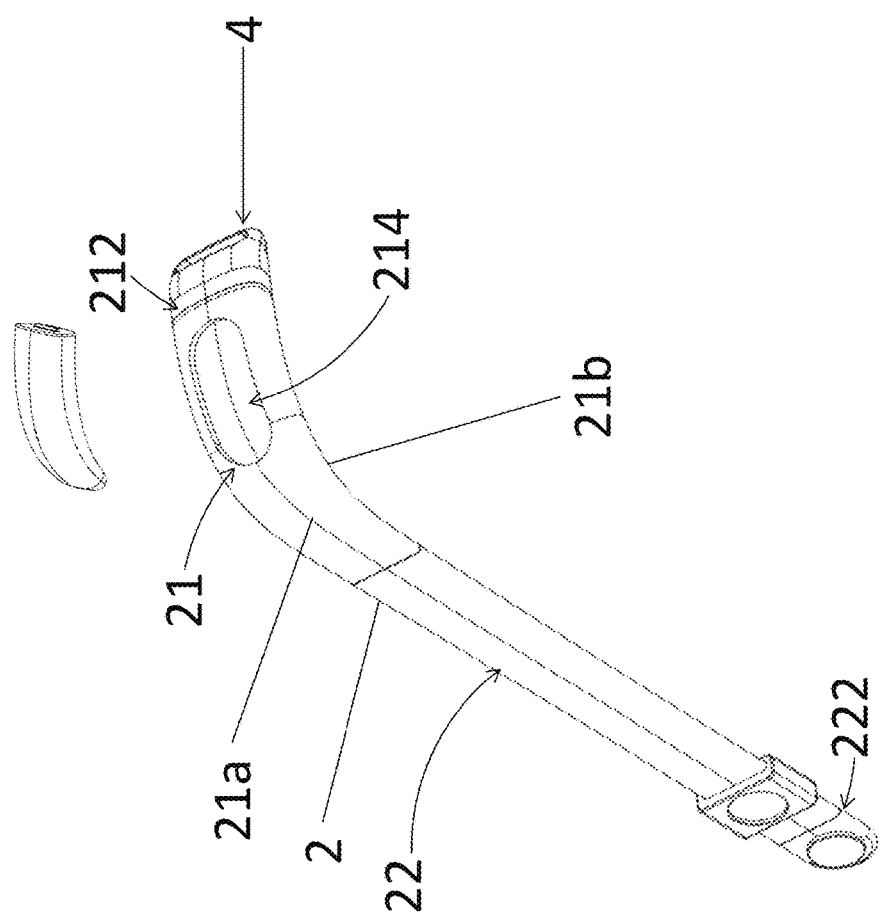
FIG. 5 is a schematic diagram illustrating a wearable device according to a third embodiment of the disclosure.
Figure 6:
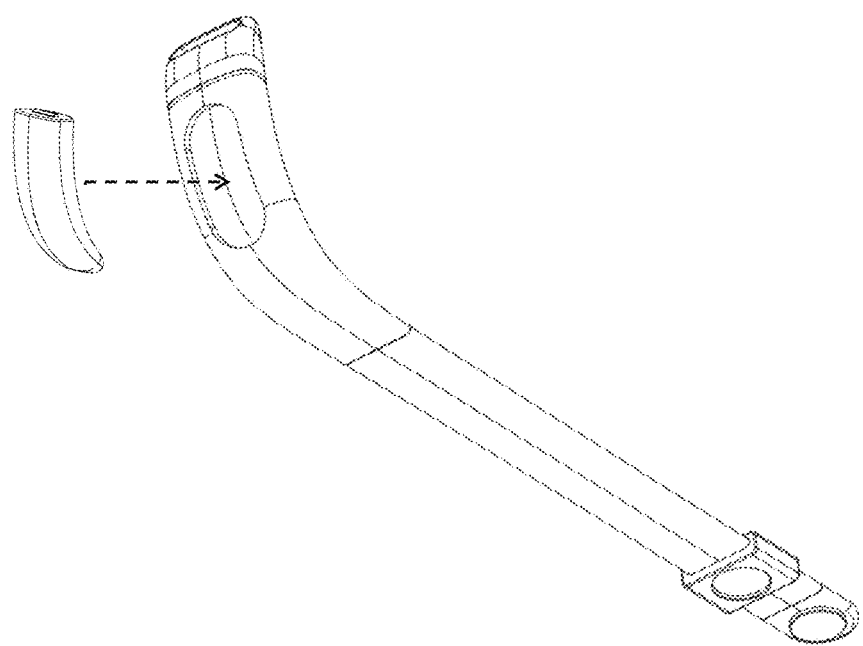
FIG. 6 is a schematic diagram illustrating a assembling process of a wearable device according to a third embodiment of the disclosure.

FIG. 5 illustrates a third embodiment of the wearable device and FIG. 6 illustrates the assembling process of the wearable device of the third embodiment. In this embodiment, when the free second end 222 of the band 22 is inserted through or into the connector 4 and fixes the band 22 to the connector 4 to form a ring, the housing 21 of the wristband 2 has an outer surface 21a facing toward the ring and an inner surface 21b opposite to the outer surface 21a, and the first opening 214 is at the outer surface 21a of the housing 21 and the connector 4 is disposed at the second end 212 of the housing 21. In this embodiment, there is free of any band between the second end 212 of the housing 21 and the connector 4.

Figure 7:
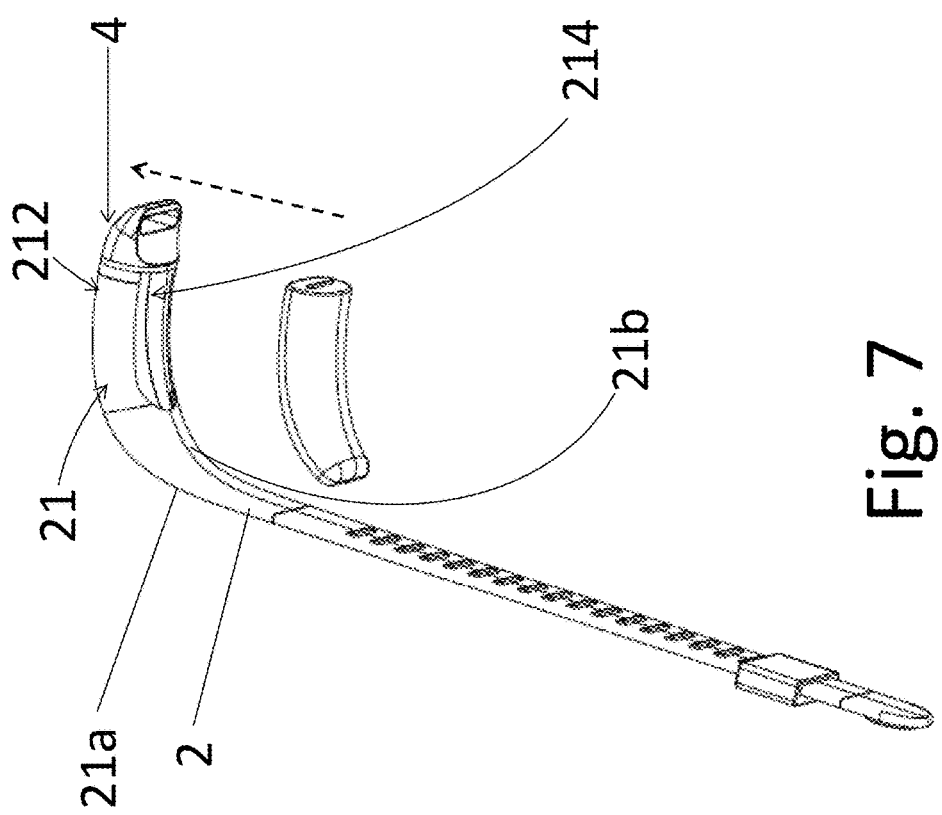
FIG. 7 is a schematic diagram illustrating a wearable device according to a fourth embodiment of the disclosure.

FIG. 7 illustrates a fourth embodiment of the wearable device. Due to the similarity between the assembling process of the wearable device of the fourth embodiment and the third embodiment, the assembling process of the wearable device of the fourth embodiment is not shown in the drawings. In this embodiment, similar to the third embodiment, the housing 21 of the wristband 2 has an outer surface 21a facing toward the ring and an inner surface 21b opposite to the outer surface 21a, and the first opening 214 is at the inner surface 21b and the connector 4 is disposed at the second end 212 of the housing 21. In this embodiment, there is free of any band between the second end 212 of the housing 21 and the connector 4.

Figure 8:
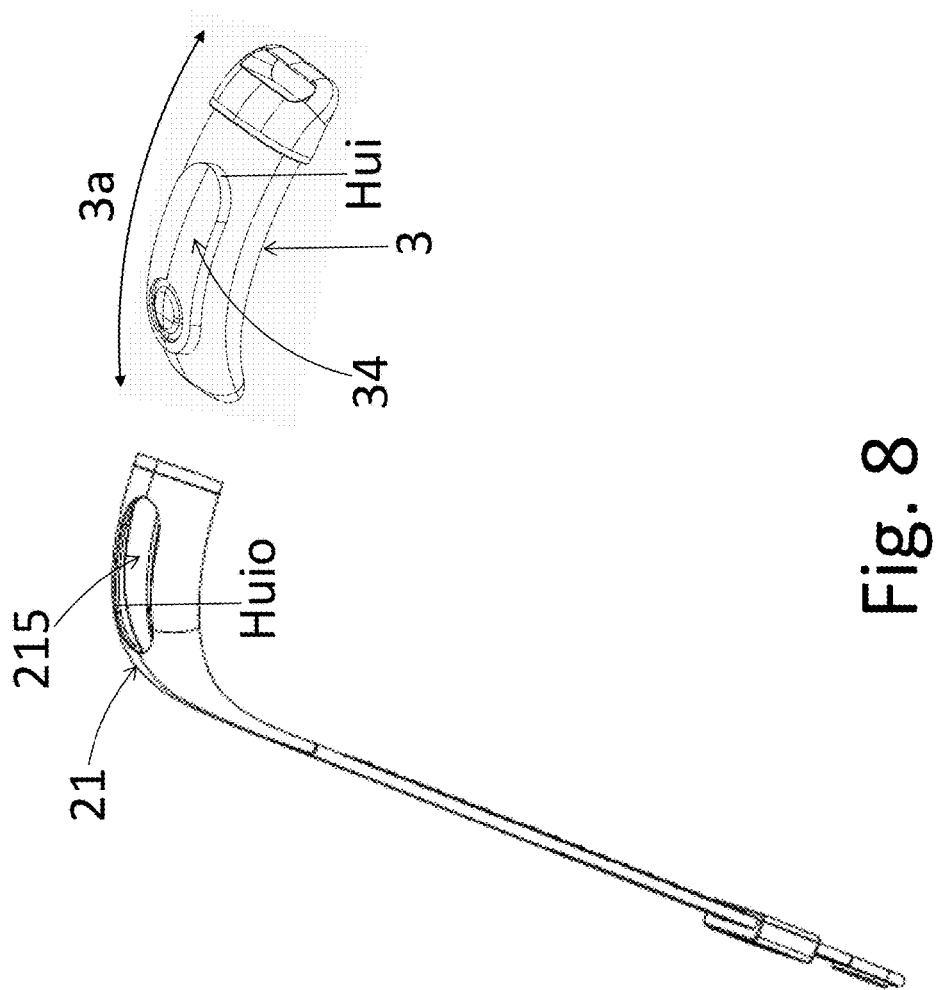
FIG. 8 is a schematic diagram illustrating a wearable device according to a fifth embodiment of the disclosure.

FIG. 8 illustrates a fifth embodiment of the wearable device. This embodiment is similar to the second embodiment but has additional features. These additional features are also applicable to the other embodiments. In this embodiment, the electronic module 3 further comprises a user interface 34 which is used to communicate to the user. More specifically, the user interface 34 can be a display, a touch panel, a button or other similar hardware which can input and/or output the information. Corresponding to the user interface 34, the housing 21 further comprises a user interface opening 215 which is used to expose the user interface 34. In this embodiment, the user interface 34 protrudes from the curved surface 3a of the electronic module 3, and the protruding height (Hui) of the user interface 34 is equal to the thickness (Huio) of the user interface opening 215. Therefore, the electronic module 3 can be more securely kept within the accommodating space. In another embodiment, the user interface 34 can be disposed on the curved surface 3a of the electronic module 3 smoothly; that is to say, the user interface 34 does not protrude from the curved surface 3a.

Figure 9:
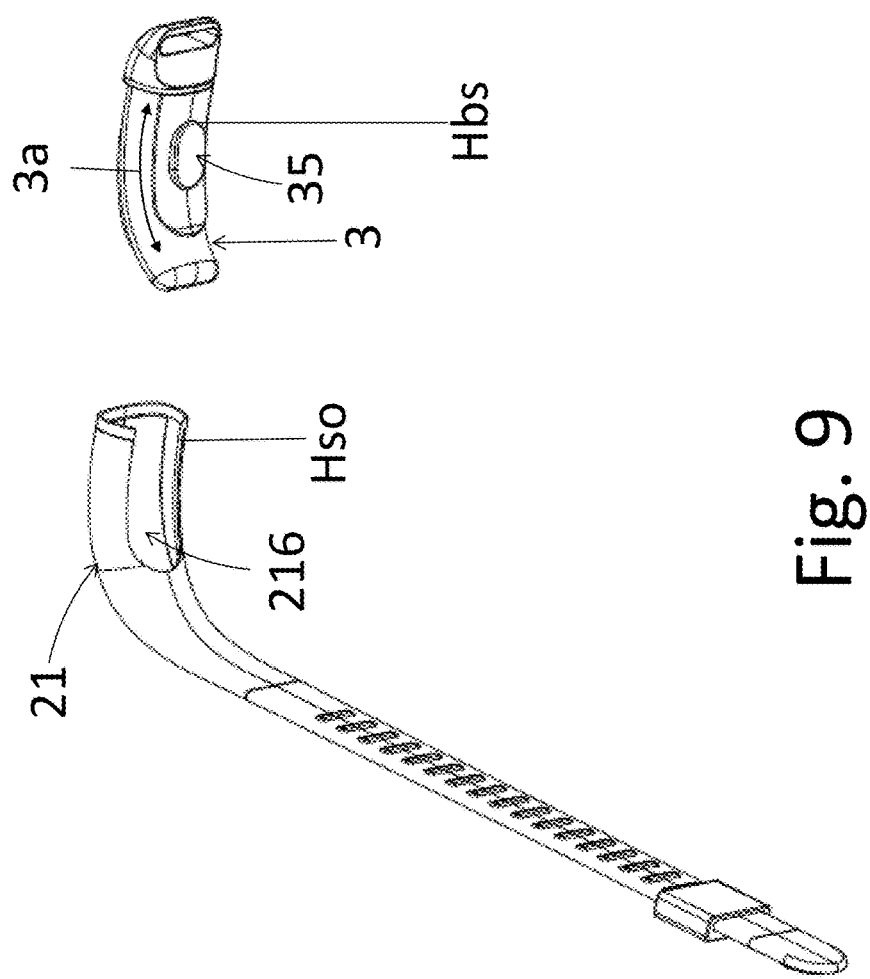
FIG. 9 is a schematic diagram illustrating a wearable device according to a fifth embodiment of the disclosure.

FIG. 9 illustrates a sixth embodiment of the wearable device. This embodiment is similar to the second embodiment but has additional features. These additional features are also applicable to the other embodiments. In this embodiment, the electronic module 3 further comprises a biological sensor 35 which is used to detect the biological information of the user. More specifically, the biological sensor can be a photoplethysmography (PPG) sensor, an Electrocardiography (ECG) sensor or any other biological sensor, and the biological information corresponds to the type of the biological sensor. Corresponding to the biological sensor 35, the housing 21 further comprises a sensor opening 216 which is used to expose the biological sensor 35 to detect the user's biological information. In this embodiment, the biological sensor 35 protrudes from the curved surface 3*a* of the electronic module 3, and the protruding height (Hbs) of the biological sensor 35 is equal to the thickness (Hso) of the sensor opening 216 Therefore, the electronic module 3 can be more securely kept within the accommodating space. In another embodiment, the biological sensor 35 can be disposed on the curved surface 3*a* of the electronic module 3 smoothly; that is to say, the biological sensor 35 does not protrude from the curved surface 3*a*.

Figure 10:
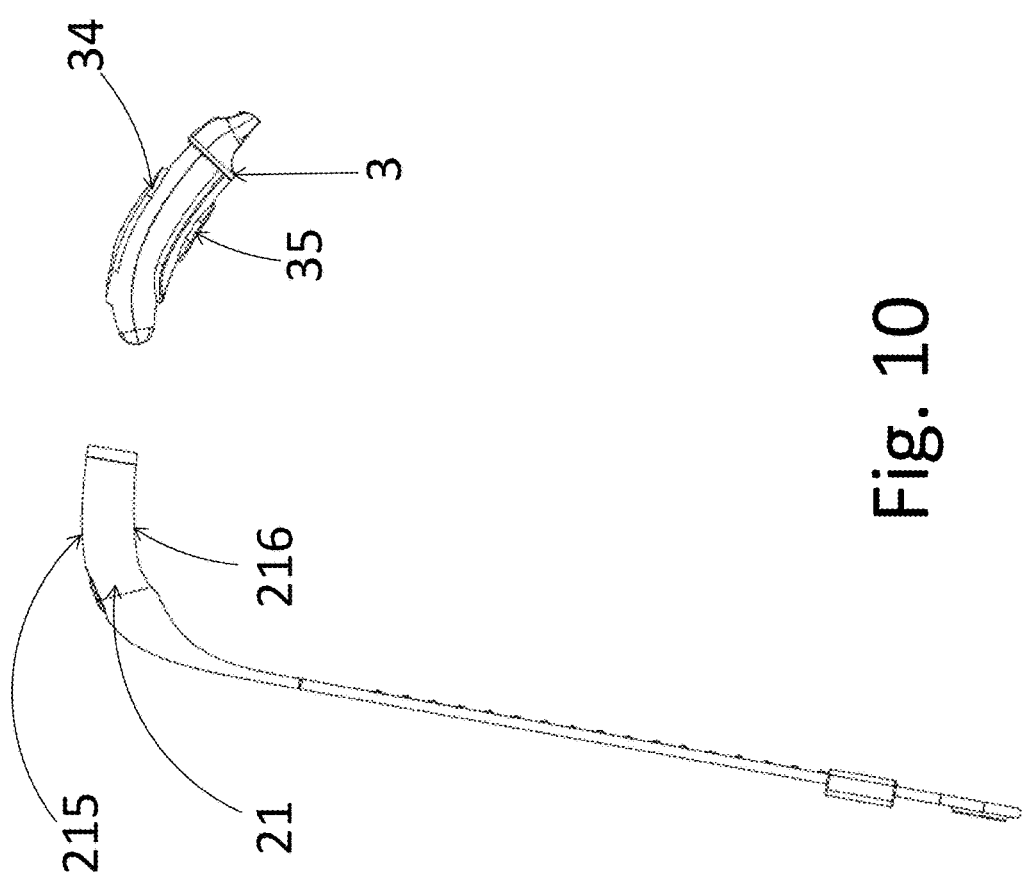
FIG. 10 is a schematic diagram illustrating a wearable device according to a sixth embodiment of the disclosure.

FIG. 10 illustrates a seventh embodiment of the wearable device. This embodiment is the combination of the fifth and sixth embodiments; that is, the electronic module 3 comprises both the user interface 34 and the biological sensor 35 and the housing 21 comprises both the user interface opening 215 and the sensor opening 216.

Figure 11:
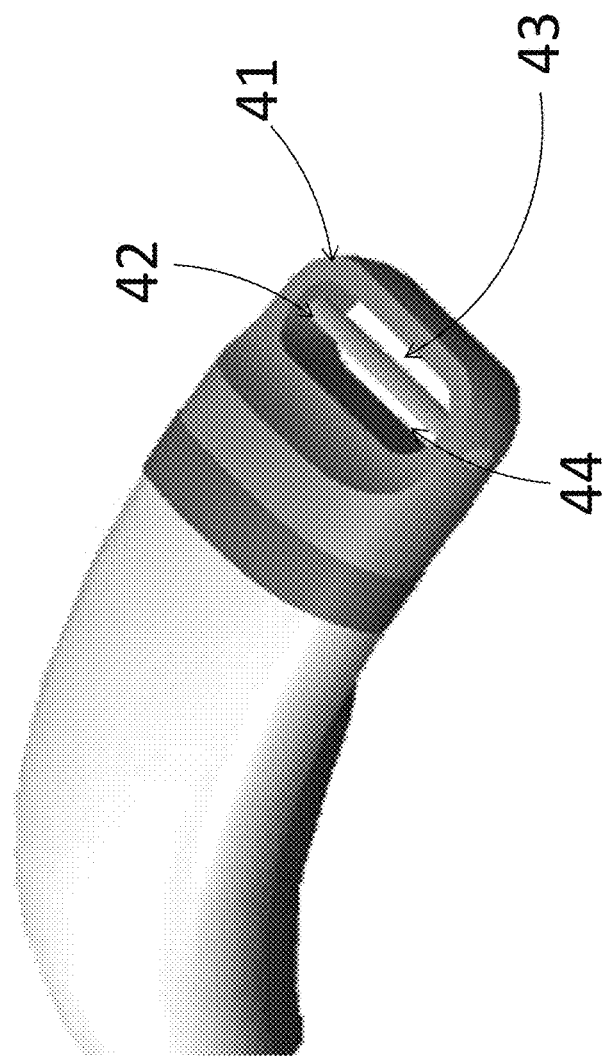
FIG. 11 is a schematic diagram illustrating a how the band fixed to the connector according to another embodiment of the disclosure.

FIGS. 11-17 illustrate various types of connector and how the band is fixed to the connector. In FIG. 11, the connector 4 comprises a ring 41 and a pillar 42, wherein the pillar 42 is disposed in the ring 41 and divides the ring 41 into square "8" shape which comprises a first connector opening 43 and the second connector opening 44. In this embodiment, the free second end 222 is inserted through the first connector opening 43 and is U-turn folded to insert through the second connector opening 44 to fix the band 22 to the connector 4.

Figure 12:
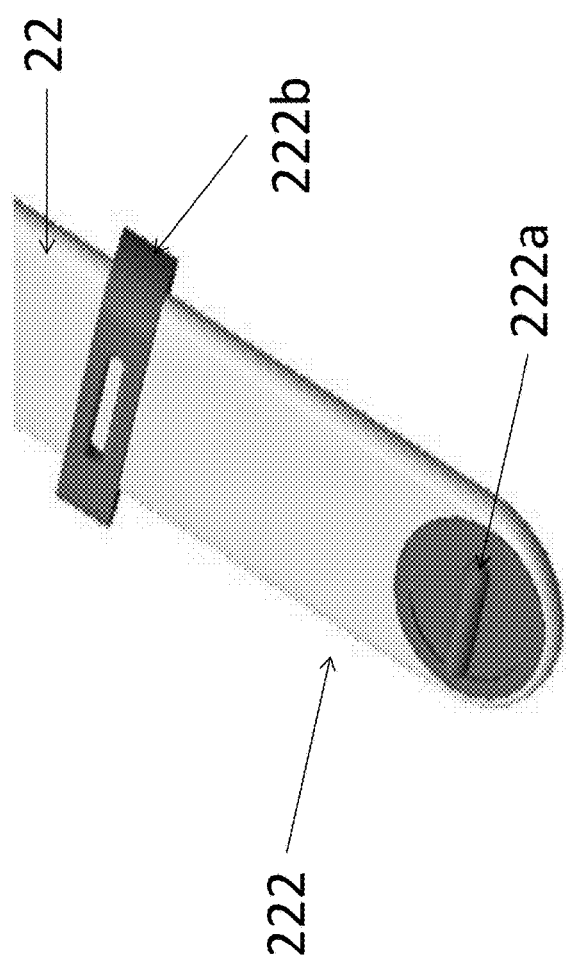
FIG. 12 is a schematic diagram illustrating how the band fixed to the connector according to another embodiment of the disclosure.

In the embodiment shown in FIG. 12, compared to FIG. 11, the band 22 further comprises a protrusion 222*a* at the free second end 222 and the notch ring 222*b*. After the free second end 222 is inserted through the second connector opening 44, the protrusion 222*a* can be stuck in the notch ring 222*b* to secure the wearable device on the wrist of the user.

Figure 13:
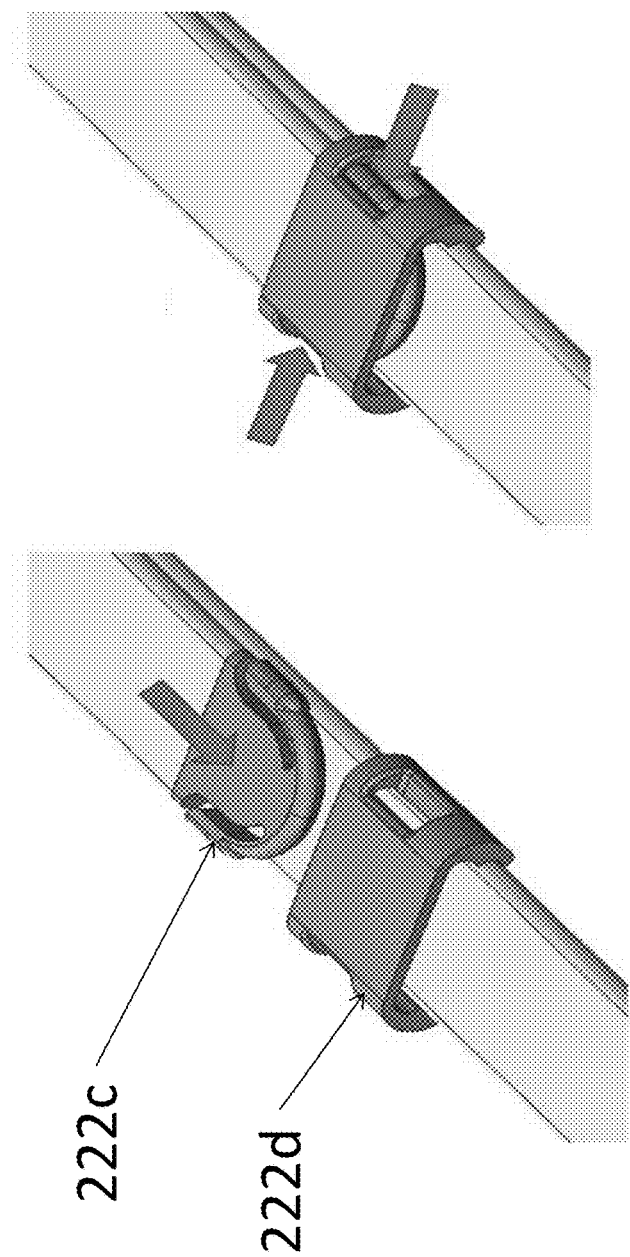
FIG. 13 is a schematic diagram illustrating how the band fixed to the connector according to another embodiment of the disclosure.
Figure 14:
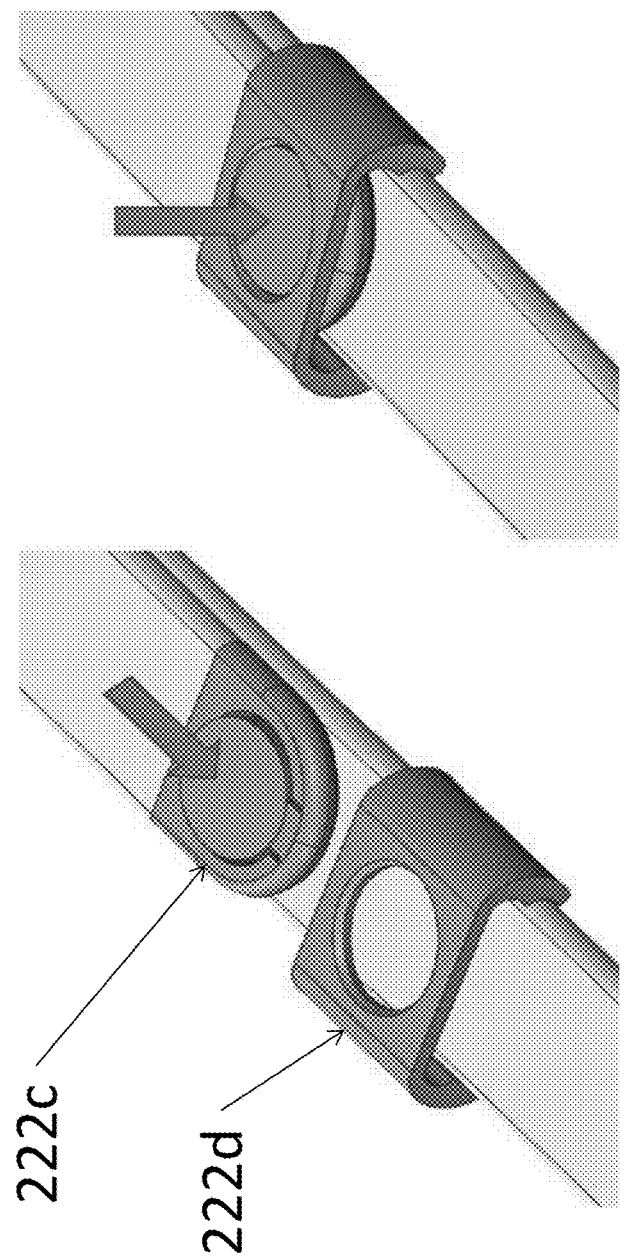
FIG. 14 is a schematic diagram illustrating how the band fixed to the connector according to another embodiment of the disclosure.

In the embodiments shown in FIGS. 13 and 14, compared to FIG. 12, the male buckle 222*c* and the female buckle 222*d*, instead of the protrusion 222*a* and the notch ring 222*b*, are used. After the free second end 222 is inserted through the second connector opening 44, the male buckle 222*c* can be connected to the female buckle 222*d* to secure the wearable device on the wrist of the user. The difference between the embodiment of FIG. 13 and the embodiment of FIG. 14 is the releasing method. The embodiment of FIG. 13 is side releasing and the embodiment of FIG. 14 is top releasing.

Figure 15:
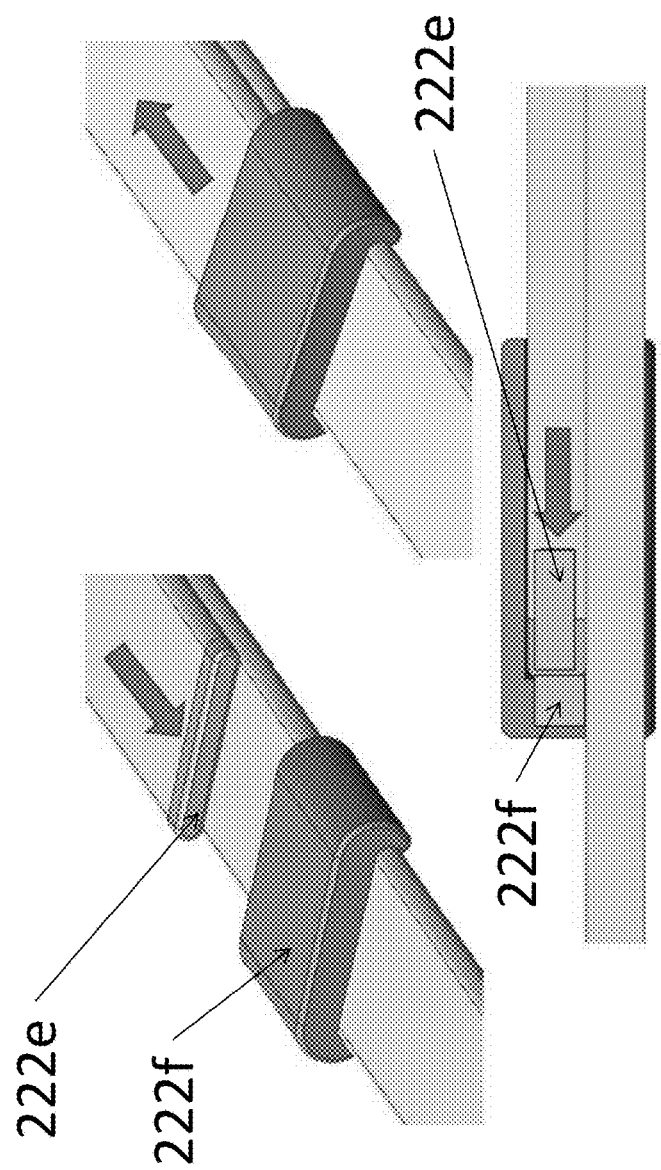
FIG. 15 is a schematic diagram illustrating how the band fixed to the connector according to another embodiment of the disclosure.
Figure 16:
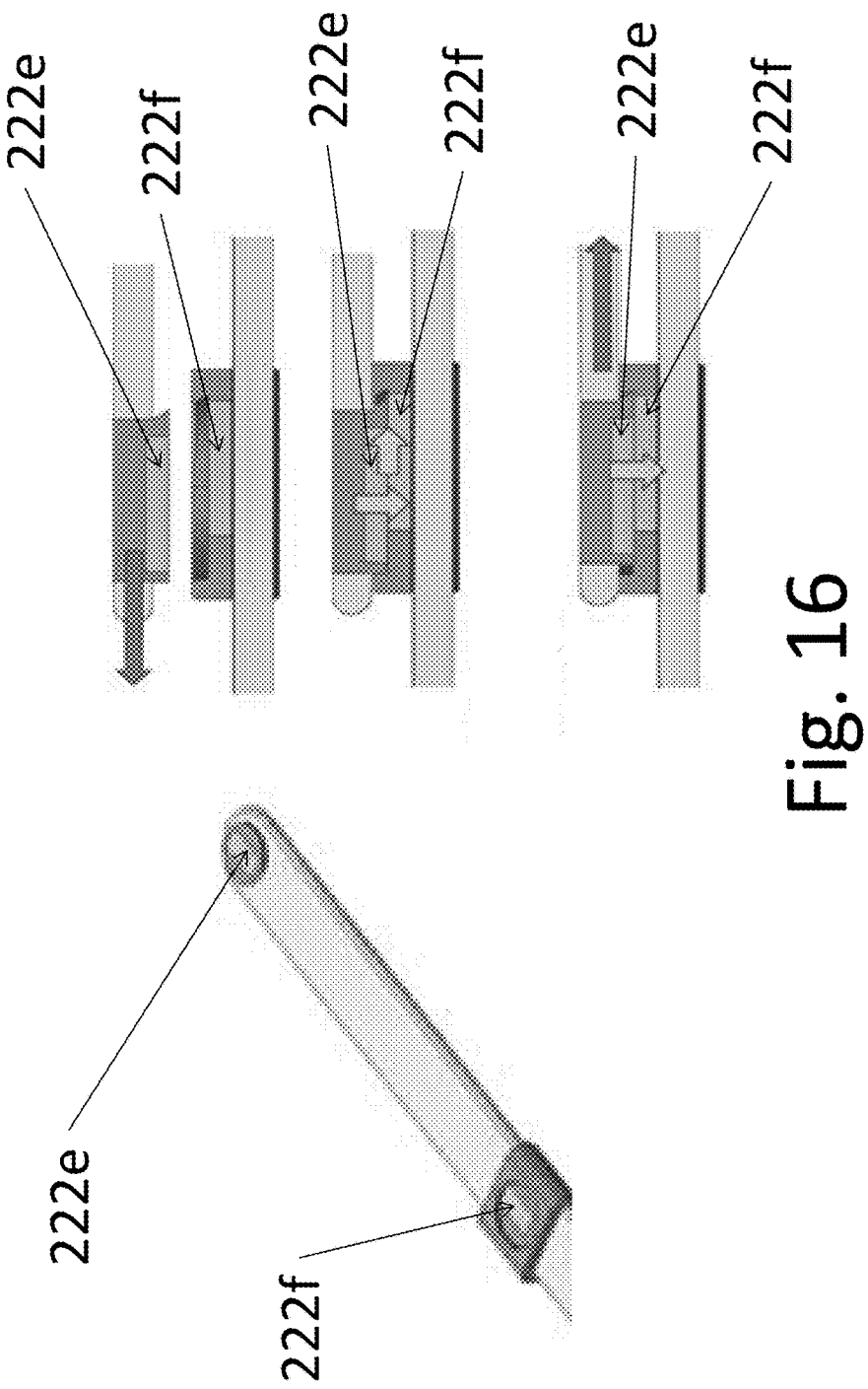
FIG. 16 is a schematic diagram illustrating how the band fixed to the connector according to another embodiment of the disclosure.

In the embodiments shown in FIGS. 15 and 16, compared to FIG. 12, the embedded magnet 222*e* and the magnet slot 222*f*, instead of the protrusion 222*a* and the notch ring 222*b*, are used. After the free second end 222 is inserted through the second connector opening 44, the embedded magnet 222*e* can be connected to the magnet slot 222*f* to secure the wearable device on the wrist of the user. The difference between the embodiment of FIG. 15 and the embodiment of FIG. 16 is the inserting method. The embodiment of FIG. 15 is side inserting and the embodiment of FIG. 16 is top inserting.

In the embodiment shown in FIG. 17, compared to FIG. 12, the hook 222*g* and the loop 222*h*, instead of the protrusion 222*a* and the notch ring 222*b*, are used. After the free second end 222 is inserted through the second connector opening 44, the loop 222*h* can be hooked by the hook 222*g* to secure the wearable device on the wrist of the user.

In view of the aforesaid embodiments, the present application offer user various types of wearable device and wristband and various ways of wearing the wearable device so as to provide the users with new and diversified wearing experiences of the wearable device.

In this disclosure, it will be understood that, although the terms "first," "second," etc., may be used herein to describe various elements, these elements should not be limited by these terms. These terms are used to distinguish one element from another. For example, a first element could be termed a second element, and, similarly, a second element could be termed a first element, without departing from the scope of the embodiments. As used herein, the term "and/or" includes any and all combinations of one or more of the associated listed items.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A wearable device, comprising:
   a wristband comprising:
      a housing having a first end, a second end, and an accommodating space between the first end and the second end; and
      a band having a first end extending from the first end of the housing, and a free second end opposite to the first end of the band;
   an electronic module disposed within the accommodating space; and
   a connector disposed either at the second end of the housing, or at a first end of the electronic module that is closer to the second end of the housing than to the first end of the housing, wherein the free second end of the band is insertable through or into the connector to fix the band to the connector,
   wherein there is free of any band between the second end of the housing and the connector and between the first end of the electronic module and the connector.

2. The wearable device according to claim 1, wherein the electronic module comprises a curved surface, and an inner surface of the housing corresponds to the curved surface.

3. The wearable device according to claim 2, wherein the electronic module has a first thickness at the first end of the electronic module, a second thickness at a second end of the electronic module, and a third thickness at a central part 33 of the electronic module which is between the first end and the second end of the electronic module, wherein the third thickness is greater than the first thickness and the second thickness, and the first thickness is greater than or equal to the second thickness.

4. The wearable device according to claim 1, wherein the housing further comprises a first opening at the second end of the housing, and the electronic module is insertable into and removable from the accommodating space through the first opening.

5. The wearable device according to claim 1, wherein when the free second end of the band is inserted through or into the connector and fixes the band to the connector to form a ring, the housing of the wristband has an outer surface faces toward the ring and an inner surface opposite to the outer surface.

6. The wearable device according to claim 5, wherein the housing further comprises a first opening at the inner surface of the housing of the wristband, and the electronic module is insertable into and removable from the accommodating space through the first opening.

7. The wearable device according to claim 5, wherein the housing further comprises a first opening at the outer surface of the housing of the wristband, and the electronic module is insertable into and removable from the accommodating space through the first opening.

8. The wearable device according to claim 1, wherein the electronic module further comprises a user interface, and the housing further comprises a user interface opening exposing the user interface.

9. The wearable device according to claim 1, wherein the electronic module further comprises a biological sensor, and the housing further comprises a sensor opening exposing the biological sensor.

* * * * *